United States Patent [19]

Hills

[11] Patent Number: 4,627,419

[45] Date of Patent: Dec. 9, 1986

[54] BLOOD PUMP APPARATUS AND METHOD

[75] Inventor: Brian A. Hills, Friendswood, Tex.

[73] Assignee: The Board of Regents, The University of Texas, Austin, Tex.

[21] Appl. No.: 645,605

[22] Filed: Aug. 29, 1984

[51] Int. Cl.⁴ .............................................. A61M 1/03
[52] U.S. Cl. ...................... 128/1 D; 422/45;
128/DIG. 12; 604/131; 604/151; 604/52;
604/4; 417/92; 623/3
[58] Field of Search ...... 128/1 D, DIG. 13, DIG. 12,
128/DIG. 3; 604/4–7, 66, 151, 122, 123, 131;
3/1.7; 422/45; 417/92, 103

[56] References Cited

U.S. PATENT DOCUMENTS

| | | |
|---|---|---|
| 2,474,665 | 6/1949 | Guarino . |
| 2,884,866 | 5/1959 | Patterson ............................ 604/153 |
| 2,954,738 | 10/1960 | Vette .................................... 604/153 |
| 3,007,416 | 11/1961 | Childs .................................. 604/153 |
| 3,043,303 | 7/1962 | Still ........................................ 604/66 |
| 3,183,908 | 5/1965 | Collins et al. . |
| 3,511,238 | 5/1970 | Von Wrangell . |
| 3,518,033 | 6/1970 | Anderson . |
| 3,568,214 | 3/1971 | Goldschmied ...................... 128/1 D |
| 3,768,496 | 10/1973 | Hills et al. . |
| 3,898,637 | 8/1975 | Wolstenholme . |
| 3,955,557 | 5/1976 | Takagi . |
| 3,967,917 | 7/1976 | Pucher et al. ....................... 417/103 |
| 3,990,444 | 11/1976 | Vial . |
| 4,131,604 | 12/1978 | Szycher .............................. 128/1 D |
| 4,212,589 | 7/1980 | Bosio ....................................... 604/4 |
| 4,250,872 | 2/1981 | Tamari . |
| 4,280,495 | 7/1981 | Lampert . |
| 4,391,598 | 7/1983 | Thompson ............................ 604/81 |
| 4,474,538 | 10/1984 | Schmid ....................... 128/DIG. 12 |
| 4,493,709 | 1/1985 | Smith ................................... 604/250 |
| 4,524,466 | 6/1985 | Hall et al. ............................ 128/1 D |
| 4,548,550 | 10/1985 | Tsuji .................................... 604/153 |

FOREIGN PATENT DOCUMENTS

| | | | |
|---|---|---|---|
| 2002190 | 8/1970 | Fed. Rep. of Germany ...... 417/102 |
| 3304486 | 8/1984 | Fed. Rep. of Germany ...... 604/131 |
| 2102412 | 4/1972 | France ................................. 604/131 |
| 1421441 | 1/1976 | United Kingdom . |

Primary Examiner—Stephen C. Pellegrino
Assistant Examiner—Mark Rooney
Attorney, Agent, or Firm—Arnold, White & Durkee

[57] ABSTRACT

A blood pump apparatus and method for pumping blood and pressure treating blood for minimizing hemolysis, platelet degradation, microthrombus and bubble formation. A blood pump apparatus for pumping and pressure treating blood comprising a flaccid chamber having an inlet for accepting fluid and an outlet for expelling fluid, a pressure housing associated with the flaccid chamber for applying pressure isotropically to dissolve or crush gaseous bubbles in the blood, an inert, heavier than blood, immiscible fluid acceptable in said flaccid chamber for displacing blood from said flaccid chamber and for drawing blood into said flaccid chamber, means for displacing said flaccid chamber and a hydraulic system and associated valves for controlling the flow of the inert fluid. A method for pumping and pressure treating blood comprising the steps of pumping an inert, heavier than blood, immiscible fluid into a flaccid chamber, inverting the flaccid chamber to position the chamber outlet below the chamber inlet for the fluid to and egrass the flaccid chamber thereby causing the blood to ingress the flaccid chamber, isotropically applying sufficient pressure for a sufficient time to dissolve or crush gaseous bubbles in the blood, ceasing the application of the pressure to the flaccid chamber, inverting the flaccid chamber to position the chamber inlet below the chamber outlet and pumping the inert fluid into the flaccid chamber thereby purging the blood from the flaccid chamber.

14 Claims, 16 Drawing Figures

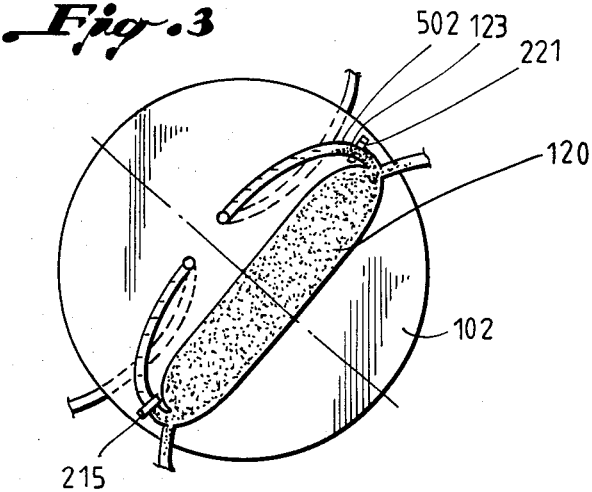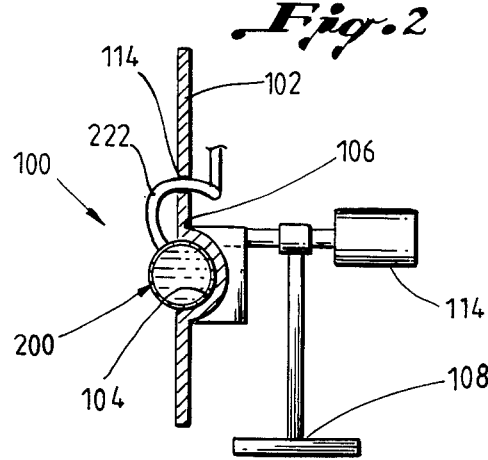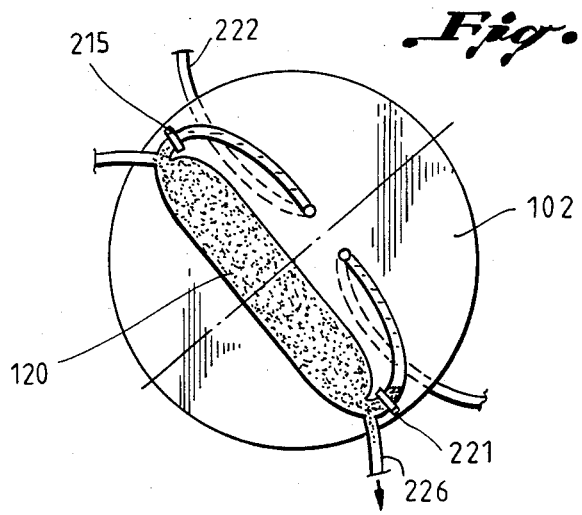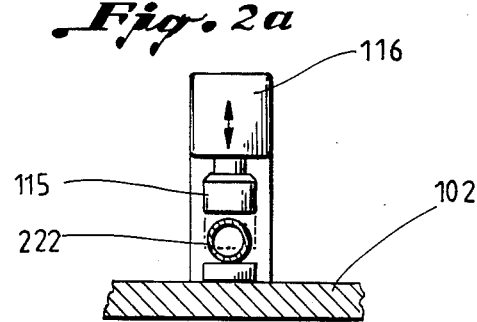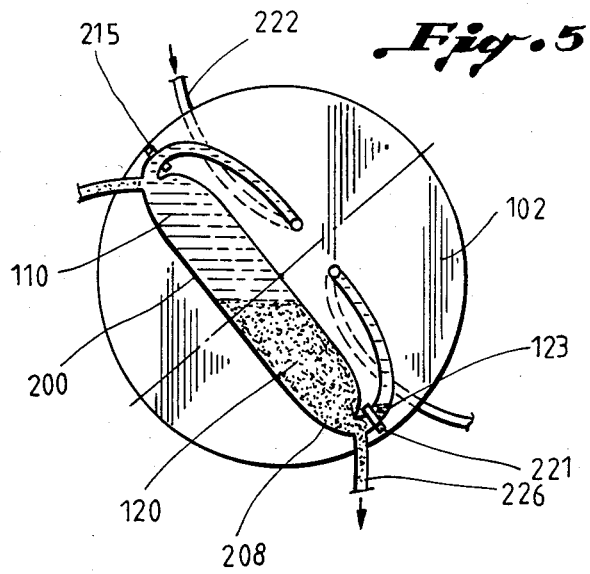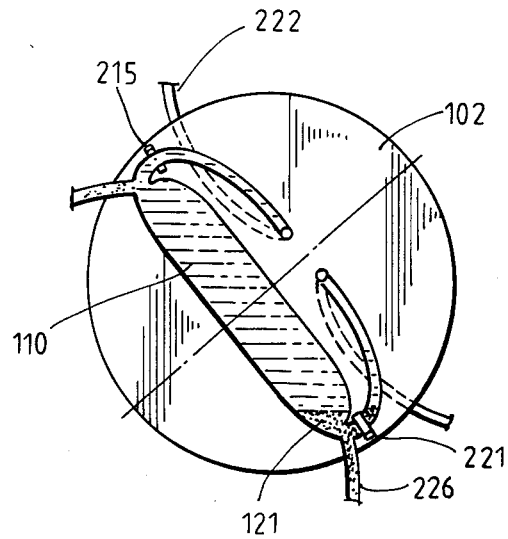

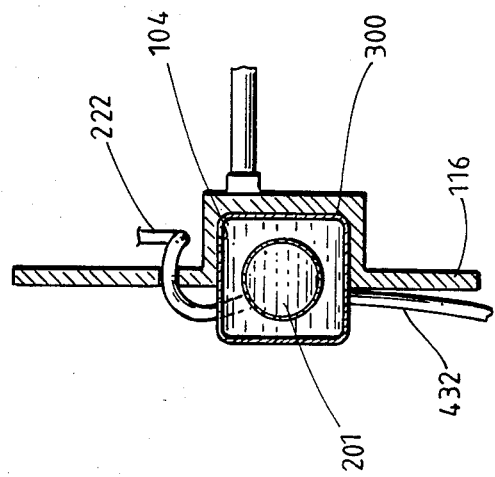
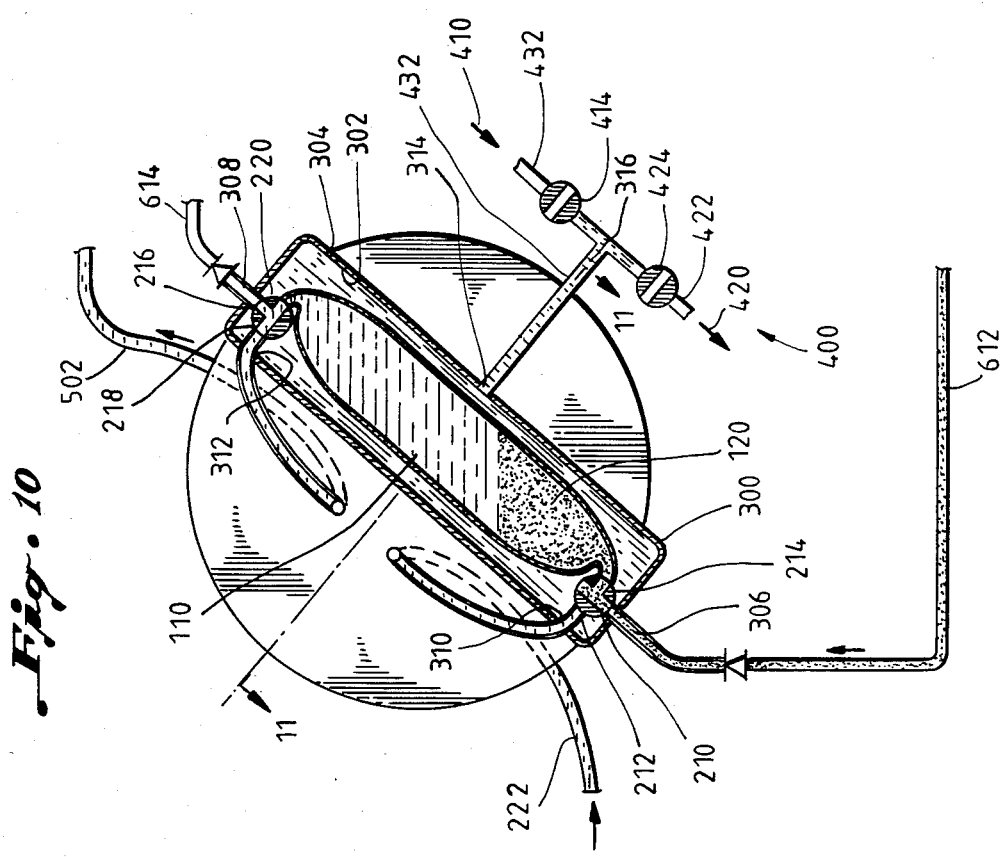

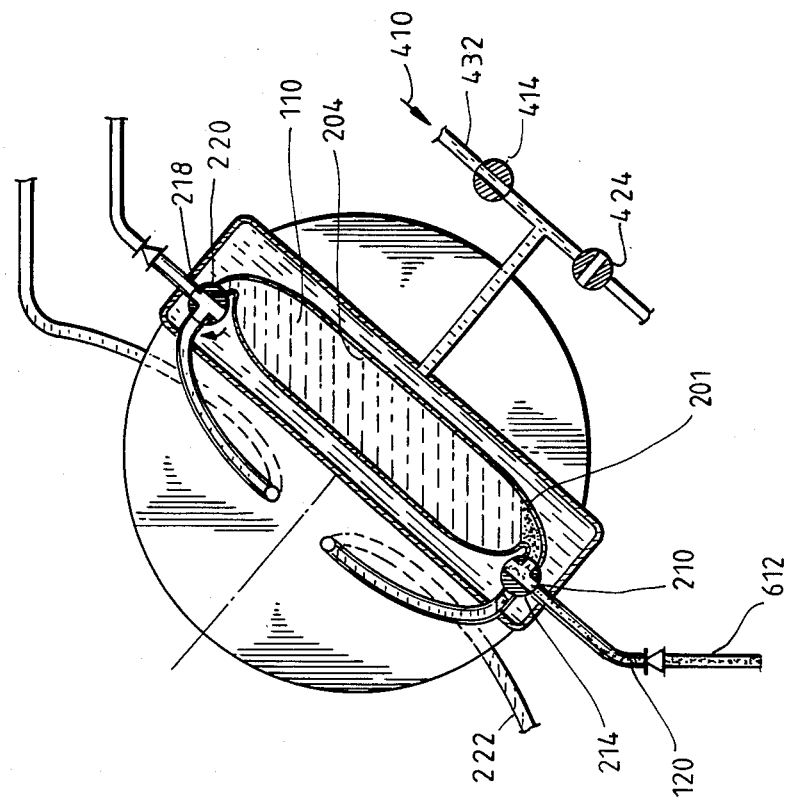
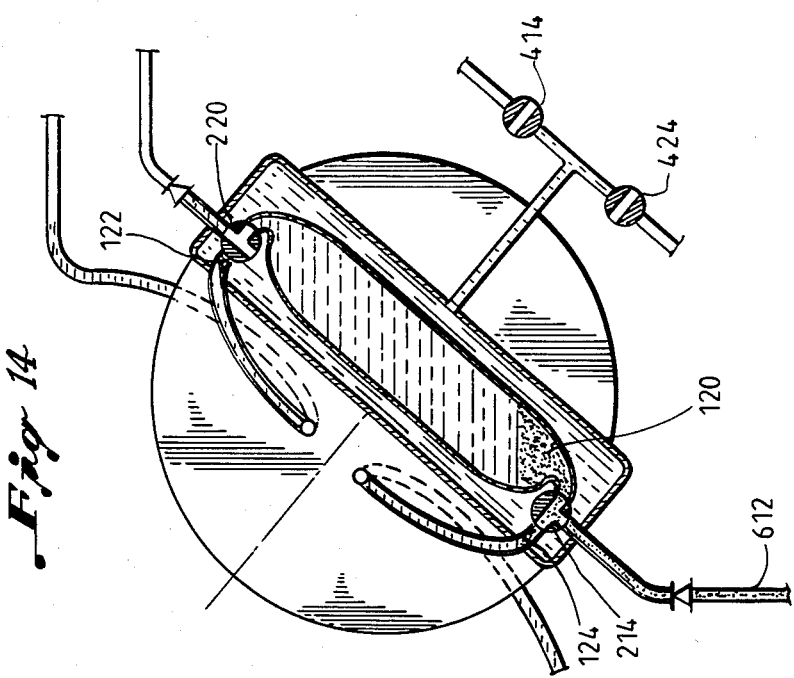

BLOOD PUMP APPARATUS AND METHOD

FIELD OF THE INVENTION

The present invention relates generally to an apparatus and method for pumping fluids and for treating fluids. More particularly, the present invention relates to an apparatus and method for accepting blood from and pumping blood to a patient as well as for minimizing hemolysis, microthrombus, platelet aggregates and bubble formation in the pumped blood.

BACKGROUND OF THE INVENTION

In many surgical procedures the heart is externally bypassed, totally or in part. In a typical procedure, venous blood is removed from the venae cavae and transported through extracorporal equipment which includes generally a pump and an oxygenator. Additionally, there may be included filters and other auxiliary equipment.

The best known pumps employed for the above purpose are the roller pump, the sack-type pump, the diaphragm pump and the piston pump. Typically, pulsatile flow is considered to be superior to non-pulsatile flow for providing the extracorporal transport of blood because it is better for perfusing the rest of the body. It is desirable to provide a flux of blood which corresponds to the rate of movement of the blood within the body of the patient.

The extracorporal movement of blood and the return of that blood to a patient has proven to be particularly difficult due to the composition of blood. Blood consists basically of a particulate-type substance and a liquid substance. The particulate-type substance are red cells or erythrocytes and the liquid is plasma. Plasma comprises, among other components, various gases, crystalloids, electrolytes and protein. The proteins are largely present in the blood as a colloidal suspension which includes platelets. The particulate red cells are suspended in the liquid plasma to form a fluid which is typically termed blood. The red cells constitute about 40% of the fluid volume of blood and normally consist of bi-concave disks about 8 microns in diameter. The red cells contain, among other components, hemoglobin, a chemical carrier for oxygen, carbon dioxide, crystalloids and electrolytes.

A blood pump for the extracorporal movement of blood must avoid damaging the blood. The walls of the blood cells are as fragile as they are important to maintaining the body's adequate metabolism. An acceptable blood pumping device should not bruise or abrade or otherwise damage the blood cells.

Generally, blood can be mechanically insulted during many phases of the pumping process. Mechanical insult to the blood can cause hemolysis or the lysis of red blood cells. Hemolysis is the rupture of the red blood cells with the liberation of their contents, specifically hemoglobin and potassium, into the plasma. Hemolysis causes adverse physiological effects upon the organs perfused with the insulted blood. The mechanical action of a pump acting on the red blood cells can reduce the colloid osmotic pressure of the red blood cells. A reduction in the colloid osmotic pressure disrupts the water retaining properties of the blood. Typically a reduction in the colloidal osmotic pressure results in edema which increases the overall fluid retention and causes a gross swelling of the patient. Denaturation of proteins, specifically platelets, can reduce the osmotic pressure of the plasma. Also, exposure of the blood to mechanical surfaces may cause coagulation of platelets and/or red blood cells to form platelet aggregates at the mechanical surface. These aggregates also reduce osmotic pressure and contribute to edema.

The coagulation also forms microthrombi or larger emboli which can lodge in arteries of smaller diameter. The lodged microthrombi decrease the blood flow and can result in varying degrees of tissue damage. Attempts to circumvent the blockage of arteries by adding an anticoagulant, such as heparin, inhibits healing at the wound surface. Red blood cells can be bruised by contact with mechanical components or by high shear stress. The bruising of red blood cells causes the cells to leak potassium ions. Potassium ions can be toxic if added to plasma in sufficient quantities. Also, white blood cells can be destroyed by mechanical insult. The destruction of white blood cells reduces a patient's ability to resist infection, and can cause numerous complicating factors.

Excessive blood transfusion is not an acceptable solution to the problem of hemolysis, edema, artery blockage, etc. The amount of blood available for transfusion is finite. A blood bank can supply only limited quantities of blood. Numerous problems and limitations exist for matching blood between critically ill patients. Also, excessive blood transfusion tends to greatly reduce the resistance of the patient to infection.

By minimizing all forms of insult to the blood, additional operating time is available for surgery. In fact, mechanical injury to blood by a pumping device almost exclusively determines the time available for surgery to the heart or to the major blood vessels in operations requiring heart bypass. For example, thoracic surgeons give various estimates for the period after which further time on by-pass seriously reduces the chances of the patient surviving. Typically, times of the order of 1½ to 2 hours are quoted. Some surgeons will even estimate the chances of survival to be as low as 50%, if there is significantly more time on by-pass using typical pumping devices.

A major problem in open-heart surgery is the inability of current technology to provide extracorporal circulation of blood without inducing hemolysis or entraining or forming gas bubbles in the blood. Typically, a pump-oxygenator system is used to provide extracorporal circulation. It is not unusual for blood circulated extracorporally using a pump-oxygenator system to be pumped to the brain of the patient without filtration or a bubble trap. Changes in personality or other detectable changes in mentation have been related to the entrainment of gaseous bubbles in the blood sent to the brain.

Hemolysis, though a problem, does not appear to significantly contribute to changes in personality or other detectable changes in mentation as experienced due to the entrainment of gaseous bubbles in the blood. Typically, extracorporal perfusion is used for periods of two to four hours during a by-pass operation with significant survival periods for patients. However, the problem of bubbles or microbubbles being entrained in the blood and returned to the patient to cause detectable changes in mentation or personality is still a critical problem.

Pump-oxygenator systems produce gaseous bubbles in the blood. Bubbles have been detected in blood from pump-oxygenator systems even when the oxygen and blood are separated by membranes. Considerable effort has been expended in producing filters for removing bubbles from the blood. Such filters have not always proven to be effective. It is believed that bubbles cannot be filtered in the same manner as solid particles, since bubbles, upon impingement on a filter, appear to deform and pass through the filter.

In addition to subtle damage to the brain characterized by changes in mentation and in personality, the entrainment of gaseous bubbles in the blood, the degradation of proteins in the plasma and platelet aggregation can cause other effects such as edema or excessive fluid problems. It is believed that an abnormally excessive accumulation of serous fluid may be collected in connective tissue due to these problems.

There is thus a need for a blood pump apparatus and method adaptable to numerous and varied medical uses, which, provides superior blood flow characteristics compatible with those in the human body, which provides minimal hemolysis and minimal microthrombosis, which reduces the formation and the entrainment of gaseous bubbles in the blood and which minimizes platelet denaturation and aggregation.

An additional feature of the present invention is to provide a blood pump apparatus and method for pressure treating blood.

Another feature of the present invention is to provide a blood pump apparatus and method which dissolves or otherwise disposes of gaseous bubbles during pumping.

A feature of a preferred form of the invention is to provide a blood pump apparatus and method which avoids the sudden interruption of the moving blood which can cause extreme negative pressures, damage to the blood and formation of bubbles.

Yet another feature of the present invention is that the blood itself is not exposed to valve closures.

An additional feature of the present invention is to provide a blood pump apparatus and method which may increase the operating time available to the surgeon without increasing the adverse physiological consequences to the patient.

Another feature of the present invention is to provide a blood pump apparatus and method that simulates the pressure and flow characteristics created by a natural heart.

Additional features and advantages of the invention will be set forth in part in the description which follows, and in part will become apparent from the description, or may be learned by practice of the invention. The objects, features and advantages of the invention may be realized and obtained by means of the instrumentality, combinations and steps particularly pointed out in the appended claims.

SUMMARY OF THE INVENTION

To achieve the foregoing features and advantages and in accordance with the purposes of the invention as embodied and broadly described herein, a blood pumping system generally comprises a flaccid chamber, means for causing the blood to flow into and out of the flaccid chamber and means for applying sufficient pressure to the blood within the flaccid chamber for dissolving or crushing gaseous bubbles in the blood. The present invention can be used exclusively to pump blood, or exclusively to pressure treat blood, or to pump and pressure treat blood.

A preferred form of pump for use in the invention is of the two phase type in which the liquid to be pumped is displaced by means of an inert liquid. The inert liquid is immiscible with, and has a different density than, the blood. In general, the inert liquid which is heavier than the blood is introduced into the flaccid chamber below the blood.

The means for moving the inert liquid into and out of the flaccid chamber comprises a hydraulic system and a system for displacing the flaccid chamber. The system for displacing the flaccid chamber provides that the flaccid chamber be tilted through an arc of approximately 90 degrees at the appropriate stages in the pumping cycle. The hydraulic system is used to force the inert fluid into the flaccid chamber and to withdraw the inert fluid from the flaccid chamber. The flaccid chamber is filled with the inert fluid when positioned with the inlets below the outlets. Thereafter, the flaccid chamber is displaced to position the outlets below the inlets. The inert fluid egresses the flaccid chamber with the aid of the hydraulic system. The egressing fluid allows the blood to ingress the flaccid chamber. The flaccid chamber is again displaced to a position with the inlets below the outlets in preparation to accept the heavier than blood inert fluid from the hydraulic system.

During the pumping cycle, a blood inlet valve and a blood outlet valve are required to obstruct the flow of blood into and out of the flaccid chamber. The valve mechanisms are operated only when the valves are occupied by the inert fluid and are never operated when the valves are in contact with the blood.

It is preferable, when the blood pump apparatus of the present invention is used to pressure treat blood, that an isotropic pressure be applied. A preferred isotropic pressure is from about 50 to about 1,000 pounds per square inch. Additionally, the preferred time duration of the isotropic pressure is approximately 1 to 30 seconds.

More specifically, one embodiment of the present invention comprises a flaccid chamber having an interior surface, an exterior surface, one or more inlets and one or more outlets, a blood inlet valve, and a blood outlet valve. An inert, heavier than blood, immiscible fluid is acceptable into the flaccid chamber for displacing blood from the flaccid chamber and for drawing blood into the flaccid chamber. Means are provided for displacing the flaccid chamber to provide either that the inlets are sufficiently above the outlets for the inert fluid to flow from the flaccid chamber allowing blood to flow into the flaccid chamber or that the outlets are sufficiently above the inlets to require the inert fluid to be pumped into the flaccid chamber causing blood to be displaced from the flaccid chamber. The blood inlet valve and the blood outlet valve are opened and closed only when occupied assed by the inert fluid.

Additional advantages are derived from the blood pump apparatus and method of the present invention by coating the interior components of the apparatus with a synthetic fluorocarbon polymer and by using a liquid fluorocarbon oligomer as the inert, heavier than blood, immiscible fluid. The synthetic fluorocarbon coating and the fluorocarbon fluid have such an affinity that a liquid film of fluorocarbon is maintained on the interior surfaces of the apparatus thus minimizing direct contact by the blood with any solid surface. The liquid film of fluorocarbon minimizes blood trauma and reduces microthrombus formations.

One method embodiment of the present invention comprises the steps of receiving blood into a flaccid chamber, applying sufficient isotropic pressure to the flaccid chamber for a time sufficient to compress the blood adequately to dissolve or crush gaseous bubbles in the blood and expelling the blood from the flaccid chamber. A preferred isotropic pressure is between about 50 and 1,000 psi for a time duration of approximately 1 to 30 seconds.

A more specific embodiment of the present invention comprises the steps of pumping an inert, heavier than blood, immiscible fluid into a flaccid chamber which has an inlet located below an associated outlet. The movement of the inert fluid is stabilized and the flaccid chamber is inverted to position the outlet below the inlet for the inert fluid to egress the flaccid chamber, thereby allowing the blood to ingress the flaccid chamber through the inlet. The movement of the blood is stabilized in the flaccid chamber. Isotropic pressure may be applied to the flaccid chamber for compressing the blood adequately to remove gaseous bubbles from the blood. The flaccid chamber is inverted to position the inlet below the outlet and the inert fluid is pumped into the flaccid chamber, thereby purging the blood from the flaccid chamber.

BRIEF DESCRIPTION OF THE DRAWINGS

The accompanying drawings illustrate a preferred embodiment of the invention and help to explain the principles of the present invention.

FIG. 2 is a cross-sectional view taken generally along the line 2—2 in FIG. 1;

FIG. 2a is a partially cross-sectional view taken generally along the line 2a—2a through the valve solenoid in FIG. 1;

FIG. 3 illustrates an embodiment of the pump of the present invention in a completely blood exhausted phase;

FIG. 4 illustrates an embodiment of the pump of the present invention in an inverted completely blood exhausted phase;

FIG. 5 illustrates an embodiment of the pump of the present invention in the blood intake phase;

FIG. 6 illustrates an embodiment of the pump of the present invention in a blood filled phase;

FIG. 10 is a partially schematic and partially structural diagram of an embodiment of the pressure treatment pump of the present invention in the blood exhaust phase;

FIG. 11 is a cross-sectional view taken generally along the line 11—11 in FIG. 10;

FIG. 14 illustrates an embodiment of the pressure treatment pump of the present invention in an inverted blood intake phase; and FIG. 15 illustrates an embodiment of the pressure treatment pump of the present invention in the pressure treatment phase.

Figure 1:
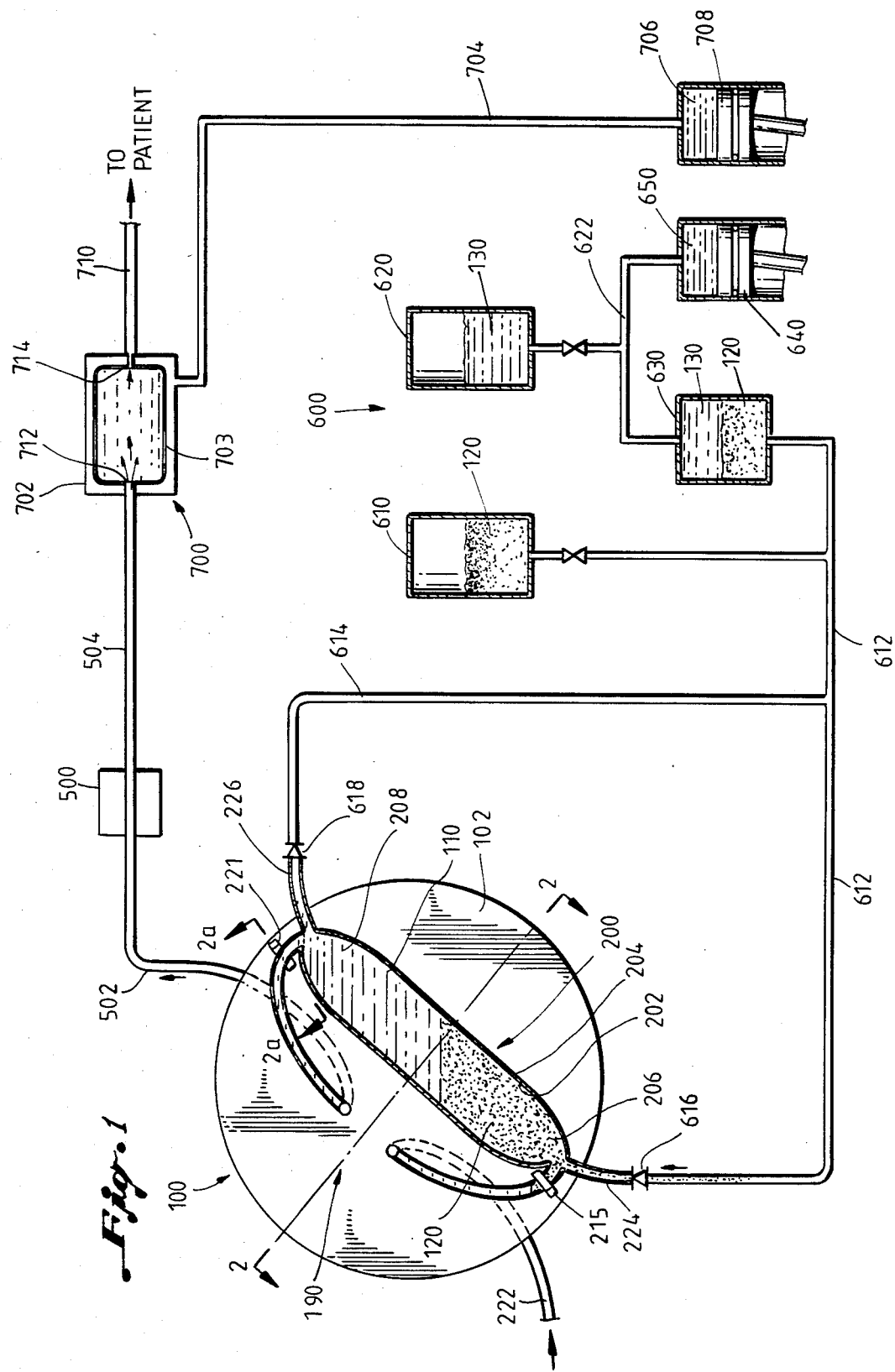
FIG. 1 is a partially schematic and partially structural diagram of an embodiment of the present invention with the pump in the blood exhaust or displacement phase, and with the valve solenoids cut away.

The above general description and the following detailed description are merely illustrative of the present invention, and additional modes, advantages and particulars of this invention will be readily suggested to those skilled in the art without departing from the spirit and scope of the invention.

DESCRIPTION OF THE PREFERRED EMBODIMENT

Reference will now be made in detail to the present preferred embodiment of the invention as described in the accompanying drawings. The blood pump 100 is comprised of a resilient, flexible or flaccid sac or chamber 200, an ultrasonic bubble detector 500, a reservoir system 600 and the pulse profile device 700. The interior components of the blood pump 100 are coated with a thin layer of a synthetic fluorocarbon polymer such as polytetrafluoroethylene ("TEFLON").

As shown in FIG. 2, the pump 100 includes a conveniently circular mounting plate 102 with a recess 104 formed therein just below a diameter of the plate 102 angled at 45° to vertical. The recess 104 conforms to the shape of the chamber 200 which is broadly tubular with tapered ends. The plate 102 is mounted at its center 106 for rotation about a horizontal axis defined by a mounting platform 108 which journals an axle 110 oscillated by a reversible stepping motor 112 or by a solenoid mechanism (not shown).

The flaccid chamber 200, as illustrated in FIG. 1, is made of a material such as "Teflon" or any resilient, flexible material that can be lined with a high molecular weight fluorocarbon polymer such as "Teflon." The flaccid chamber 200 has an interior surface 202, an exterior surface 204, a fluid entrance end 206 and a fluid exit end 208. The inlet valve 215 and outlet valve 221 may be simple clamp-type valves. The blood conduit 222 and the return conduit 502, which extend through supporting apertures 114 in the plate 102, are either totally open or totally closed by the inlet valve 215 and the outlet valve 221, respectively.

The inlet valve 215 and the outlet valve 221 can be of a type which physically distort the conduits 222 and 502 to totally obstruct the passage of any fluid therethrough. As shown in FIG. 2a, the valve 215, 221 may include a wedge 115 displaced toward or away from the conduit 222 or 502 by a solenoid 116 or mechanical linkage (not shown) mounted on the plate 102. A pad 117 may be located between the conduit 222, 502 and the plate 102. The conduits 222 and 502 can be made of any resilient material which will return to the original configuration when not clasped by the valves 215 and 221, respectively. Thus the valves 215 and 221 may be operable by clamping the conduits 222 and 502 shut against the plate 102, under the control of a suitable operator, such as the solenoids.

A separable unit 199 comprises the flaccid chamber 200, a portion of the blood conduit 222, a portion of the return conduit 502, the inlet valve 215, the outlet valve 221, the entrance conduit 224 and the exit conduit 226. The unit 199 can be used to pump blood during a single operation and then discarded. The unit 199 can also be sterilized between uses and maintained for a period of time corresponding to the duration of the material components. Alternatively, the unit 199 may include a disposable inner liner (not shown).

The reservoir system 600 is used to inject into and withdraw from the flaccid chamber 200 a physiologically inert fluid 120 which has a density different from that of blood, has a low viscosity, and is immiscible with blood, such as a liquid, low molecular weight fluorocarbon oligomer. A suitable fluorocarbon oligomer is FC-80, made by 3-M Company, which is essentially perfluoro-butyltetrahydrofuran and isomers thereof with a density of 1.7 gm/cc (compared to 1.0 gm/cc for blood). In a preferred embodiment of the reservoir system 600, a piston and reservoir system is utilized. The inert fluid reservoir 610 is used to supply sufficient quantities of the physiologically inert fluid 120 to the flaccid chamber 200 during the operation of the blood pump 100.

A saline reservoir 620 provides saline solution 130 to the reservoir 630. The piston 640 reciprocates within the chamber 650 to move the saline 130 through the conduit 622. When the piston 640 is advanced in the chamber 650, the saline solution 130 advances through the conduit 622 and into the reservoir 630. The incoming saline solution 130 forces the inert fluid 120 through the feed conduit 612 and through the one-way valve 616 into the entrance conduit 224. When the piston 640 travels downwardly within the chamber 650, the saline solution 130 is pulled into the chamber 650 through the conduit 622. The saline solution 130 is extracted from the reservoir 630 causing the inert fluid 120 to enter the reservoir 630.

The inert fluid 120 may be pumped directly, if desired, and the saline solution may be eliminated. The use of saline solution may provide economies in that less inert fluid be used and pump leakage results only in loss of the inexpensive saline solution.

The inert fluid 120 entering the reservoir 630 is acquired primarily from the flaccid chamber 200 by passing through the exit conduit 226, the one-way valve 618 and the recycle conduit 614. Also, a portion of the inert fluid 120 entering the reservoir 630 can be acquired from the inert fluid reservoir 610 if sufficient inert fluid 120 is not available from the flaccid chamber 200 for some reason (e.g., a short pump cycle). The reservoir system 600 is capable of supplying sufficient inert fluid 120 to fill the flaccid chamber 200 as well as to receive the inert fluid 120 from the flaccid chamber 200.

The pulse profile device 700 is used to create a pressure-time profile which corresponds to the frequency, pressure and stroke volume of the patient's heart. The pulse profile device 700 comprises the after-chamber 702, the piston 708, the chamber 706, the conduit 704 and the conduit 710. Typically, the blood exhausted from the flaccid chamber 200 passes through the return conduit 502 to be evaluated for bubbles by the ultasonic detector 500. The ultrasonic detector 500 detects the flux of any bubbles entrained in the blood 110 prior to passing through the exit conduit 504 and provides a suitable warning indication. Thereafter, the blood passes through the conduit 504 and into the after-chamber 702.

The after-chamber 702 can perform desired physical changes upon the received blood to more adequately prepare the blood to correspond with that of the patient. The after-chamber 702 can be equipped with a heating unit to provide that the blood passed to the patient is at the same temperature as the blood in the patient. Additionally, a pressure-time profile for the blood passed to the patient can be created to correspond with the pressure-time profile that would exist with the patient's heart or that would be most conducive to the conditions of the patient. A pressure-time profile can be created using a cam driven piston 708, acting as a pulse generator, to apply pressure to the after-chamber 702 through the conduit 710. The varying pressure within the after-chamber 702 deforms the flexible, resilient chamber 703 to adjust the flow of fluid passing through the conduit 710. For example, the pulse profile device 700 may produce 60–80 pulses per minute.

The pulse profile device 700 also operates to convert the high volume pulses created by the pump 100 and collected in the chamber 702, into a series of smaller volume pulses spaced in time over the entire pumping cycle. The chamber 703 has a large inlet port 712 and a much smaller outlet port 714 so that the blood is collected under pressure within the chamber 703 which is resiliently distended by the blood.

FIG. 1 illustrates the blood pump 100 of the present invention in the blood exhaust phase. The piston 640 is advancing in the chamber 650 causing the inert fluid 120 to pass through the feed conduit 612, through the one-way valve 616, through the entrance conduit 224 and into the flaccid chamber 200. The inlet valve 215 is closed preventing the inert fluid 120 from passing into the blood conduit 222. The pressure on the fluid created by the piston 640 advancing in the chamber 650 causes a back-pressure in the recycle conduit 614 to secure the one-way valve 618 thus preventing any flow therethrough. The blood outlet valve 221 is open. Therefore, as the inert fluid 120 is forced into the flaccid chamber 200 the blood 110 is forced out of the flaccid chamber 200 through the outlet valve 221, into the return conduit 502 and to the patient.

FIG. 3 illustrates the blood pump 100 of the present invention in a completely blood exhausted phase. The flaccid chamber 200 is completely filled with the inert fluid 120. Additionally, a small portion of the return conduit 502 is sufficiently filled with the inert fluid 120 to a point just beyond the blood outlet valve 221. At this point, the piston 640 stops advancement into the chamber 650. As illustrated in FIG. 2, the blood outlet valve 221 should be closed only when it is filled with the inert fluid 120. The blood outlet valve 221 should not close when blood 110 is in the valve. A slug 123 of the inert fluid 120 is separated from the main portion of the inert fluid 120 by blood outlet valve 221. Thus, the blood is never present at the closure site which eliminates potential injury to the blood.

FIG. 4 illustrates the pump of the present invention in an inverted completely exhausted phase. FIG. 4 is an illustration of the exact configuration illustrated in FIG. 3 with the exception that the pump 100 has been rotated 90 degrees in a clockwise direction. The plate 102 is rotated 90° clockwise by the motor 112, to the position shown in FIG. 4. With the blood inlet valve 215 open, the piston 640 can then be withdrawn from the chamber 650 to cause the inert fluid 120 to pass through the exit conduit 226 and back into the reservoir system 600.

FIG. 5 illustrates the pump 100 of the present invention in the blood intake phase. The blood inlet valve 215 is open. Blood is passing through the blood conduit 222, through the open inlet valve 215 and into the flaccid chamber 200. As the blood 110 passes into the flaccid chamber 200, the inert fluid 120 is caused to pass from the flaccid chamber 200 through the exit conduit 226.

The blood continues to fill the chamber 200 until only a small quantity 121 of inert fluid 120 is left in the exit end 208 of the flaccid chamber 200, as shown in FIG. 6. The outlet valve 221 closes to separate the quantity of inert fluid 120 from the slug 123 of the inert fluid 120. Inlet valve 215 can still be open at this point. The valves 215 or 221 are only closed when they are rotated to their lowest points and when they are filled with inert fluid 120.

Figure 7:
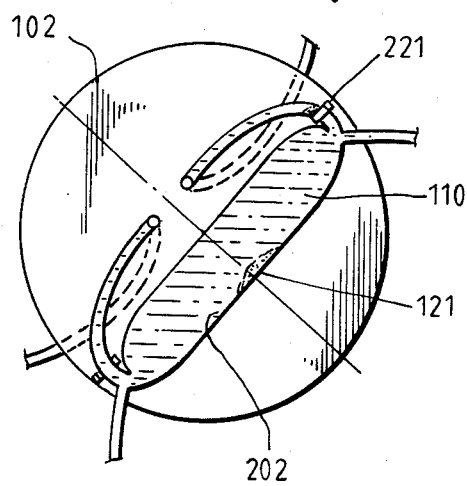
FIG. 7 illustrates an embodiment of the pump of the present invention in an inverted blood filled phase.

FIG. 7 illustrates the pump 100 of the present invention again in a blood intake phase. The pump 100 has been rotated 90 degrees counterclockwise to the original position shown in FIG. 1 and the valve 221 has been opened. After rotation, the portion of the inert fluid 120 that was located in the exit end 208 of the flaccid chamber 200, i.e., the slug 121, is caused by the acceleration of gravity to flow down the interior surface 202 of the flaccid chamber 200. In FIG. 7, the slug 121 is illustrated flowing down the interior surface 202 of the flaccid chamber 200 immediately following the 90 degree rotation of the pump 100.

Figure 8:
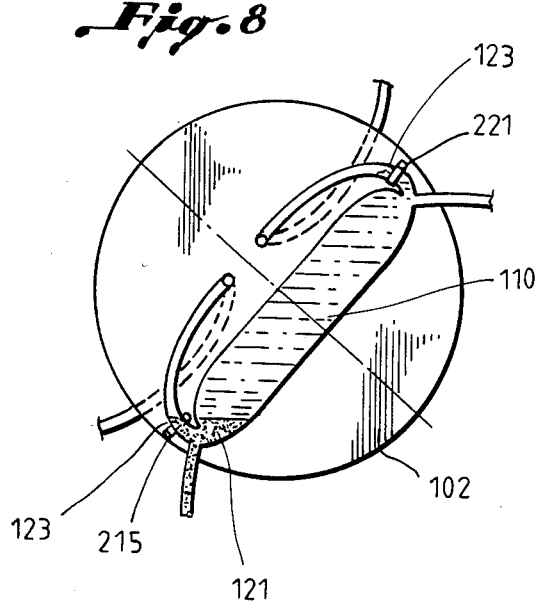
FIG. 8 illustrates an embodiment of the pump of the present invention in a completely blood filled phase with the blood inlet valve occupied by an inert fluid.

FIG. 8 illustrates the pump 100 in a completely blood filled phase. The blood inlet valve 215 is initially open and is completely filled by the inert fluid 120. The blood inlet valve 215 is closed when filled with the inert fluid 120 so that the blood 110 cannot be engaged. A slug 123 of inert fluid 120 is trapped above the inlet valve 215.

Figure 9:
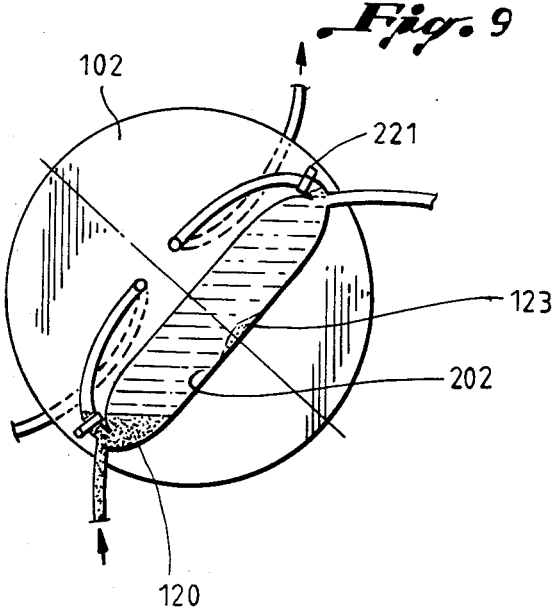
FIG. 9 illustrates an embodiment of the pump of the present invention in the blood exhaust and inert fluid intake phase.

FIG. 9 illustrates the pump 100 in a completely blood filled phase similar with the blood outlet valve 221 opened. The slug 123, previously held above the valve 221, acting under the force of gravity, descends the interior surface 202 of the flaccid chamber 200 to join with the inert fluid 120. The piston 640 can be advanced in the chamber 650 to force the inert fluid 120 into the flaccid chamber 200. As the inert fluid 120 is passed into the flaccid chamber 200, the blood 110 is forced to exit by the blood outlet valve 221 and through the return conduit 502.

A pressure treatment pump 101, shown in FIGS. 10 and 11 is comprised of the flaccid chamber 201, the rigid pressure housing 300, and the pressurization system 400, as well as the ultrasonic bubble detector 500 and the reservoir system 600 shown in FIG. 1.

The flaccid chamber 201, as illustrated in FIG. 10, is similar to the chamber 200 except that the inlet valve 214 of chamber 201 has two inlet-ports 210 and 212 and the outlet valve 220 has two outlet ports 216 and 218. The inlet port 210 is smaller in cross sectional area than the inlet port 212. The outlet port 216 is smaller in cross sectional area than the outlet port 218. The valves 214 and 220 are advantageously 3-port ball valves, operable by solenoids or mechanical leakages (not shown).

The pressure housing 300, mounted in the recess 114 of mounting plate 116, encloses the flaccid chamber 201, as shown in FIG. 11. The pressure housing 300 has an interior surface 302 and an exterior surface 304. The interior of the housing 300 may be heated. The pressure housing 300 has a sealed pressurization port 314 through which a pressurization fluid 316 can flow. The pressurization fluid 316 acts upon the flaccid chamber 201 to isotropically compress the flaccid chamber 201. The fluid 316 may be either a liquid or a gas but advantageously a gas, such as compressed air is used as the fluid 316.

The pressure housing 300 has apertures 306, 308, 310 and 312 to provide connections with the flaccid chamber 201. The aperture 306 provides an entrance for the feed conduit 612 from the reservoir system 600. The feed conduit 612 is connected to the inlet port 210 in the inlet valve 214. The aperture 308 provides a passage for the recycle conduit 614 from the reservoir system 600. The recycle conduit 614 is connected to the outlet port 216 in the valve 220. The aperture 310 provides a passage for the blood conduit 222 from the patient. The blood conduit 222 is connected to the inlet port 212 in the inlet valve 214. The aperture 312 provides a passage in the pressure housing 300 for the return conduit 502. The return conduit 502 connects the outlet port 218 in the valve 220 with the ultrasonic bubble detector 500.

The pressurization system 400 is used to create an isotropic pressure within the pressure housing 300. A pressurization fluid 316 is supplied from the pressurization system 400 to the pressure housing 300 through the conduit 432 and into the pressure housing 300 via the pressurization port 314. A predetermined and programmable sequence of pressure differentials can be maintained against the flaccid chamber 201 using the pressurization fluid 316. Thus, small variations in pressure which need to be applied to the flaccid chamber 201. For example, the isotropic pressure can be maintained on the flaccid chamber 201 which corresponds exactly to the venous pressure for the patient.

A back pressure supply 420 can be used to maintain a fixed pressure in the high pressure housing 300. The back pressure supply 420 is connected to the pressure housing 300 by the back pressure valve 424 which connects the back pressure conduit 422 with the conduit 432. An advantageous valve 424 is a two-way rotary valve which can be in an open position or a closed position only. However, any valve having the required operating characteristics can be used.

A preferred embodiment of the present invention provides that the pumped blood can be pressure treated. High pressure is applied to the flaccid chamber 201 in the pressure housing 300 by a high pressure supply 410 activating the pressurization fluid 316. Any high pressure supply can be utilized that provides the required operating characteristics. The high pressure supply 410 is connected to the pressure housing 300 by the conduit 432, high pressure valve 414 and the high pressure conduit 412. One preferred high pressure valve 414 is a two-way rotary valve which can be in an open position or a closed position only. However, any high pressure valve having the required operating characteristics can be used.

FIG. 10 illustrates the pressure treatment pump 101 of the present invention in an exhaust phase. The blood 110 is shown being forced out of the flaccid chamber 201 by the inert fluid 120. The inert fluid 120 is caused to enter flaccid chamber 201 by the piston 640 advancing in the chamber 650. The blood 110 flowing out of the flaccid chamber 201 passes through the blood outlet port 218 in the three-way outlet valve 220. The blood outlet port 218 is significantly larger than the outlet port 216. The size of the outlet ports 216 and 218 as well as the density of the inert fluid 120 causes the path of least resistance of the blood 110 to be through the outlet port 218 and into the conduit 502. The blood 110 passes through the conduit 502 and to the ultrasonic bubble detector 500.

Figure 12:
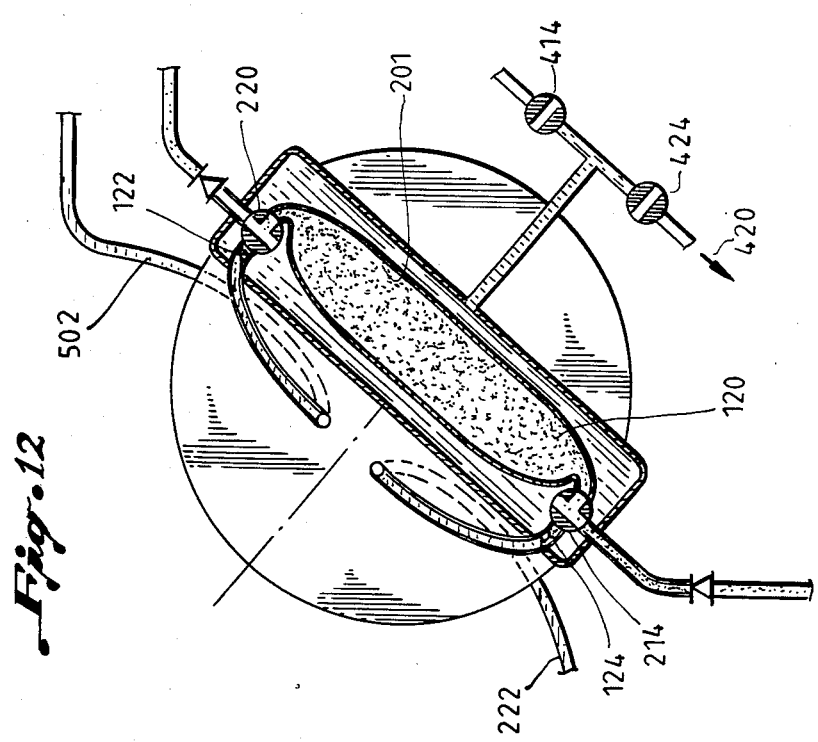
FIG. 12 illustrates an embodiment of the pressure treatment pump of the present invention in a completely blood exhausted phase.

FIG. 12 illustrates a preferred embodiment of the pressure treatment pump 101 of the present invention in a completely blood exhausted phase. The flaccid chamber 201 is completely filled with the inert fluid 120. The fluid 120 has even passed through the outlet valve 220 and slightly into the conduit 502. After the outlet valve 220 is completely immersed in the fluid 120, the outlet valve 220 is closed with respect to conduit 502 to prevent significant quantities of the fluid 120 from passing into the conduit 502. However, a slug 122 of the fluorocarbon 120 remains in the conduit 502. The inlet valve 214 has remained closed with respect to the conduit 222. A slug 124 of the inert fluid 120 remains in the blood conduit 222. The orientation of the flaccid chamber 201 provides that the outlet valve 220 is at a position above the inlet valve 214.

Figure 13:
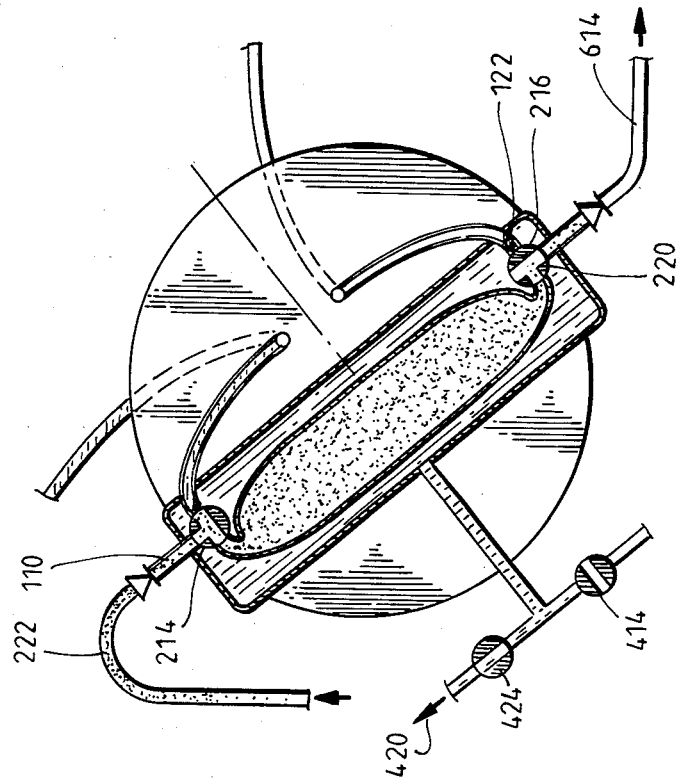
FIG. 13 illustrates an embodiment of the pressure treatment pump of the present invention in an inverted completely blood exhausted phase.

FIG. 13 illustrates the pressure treatment pump 101 in an inverted blood exhausted position just prior to the intake phase. The pressure treatment pump 101 has been rotated clockwise 90 degrees. The inlet valve 214 is now oriented to pass blood from the patient through the blood conduit 222 into chamber 201. The back pressure supply 420 is activated by the back pressure valve 424. The back pressure supply 420 maintains a desired pressure within the pressure housing 300 and upon the flaccid chamber 201. The pressure on the flaccid chamber 201 can be maintained at the pressure of the venous system of the patient by the back pressure supply 420. Therefore, the blood 110 enters the flaccid chamber 201 under substantially the same pressure as the venous system of the patient or against whatever pressure the surgeon may desire.

The inlet valve 214 changes position only when filled with the inert fluid 120. When the inlet valve 214 is opened to connect conduit 222 with the flaccid chamber 201, the fluid 120 is extracted from the flaccid chamber 201 by the piston 640 being withdrawn from the chamber 650. The inert fluid 120 passes through the outlet port 216 in the outlet valve 220 and into the recycle conduit 614. With this opening of the outlet valve 220, the slug 122 is united with the main body of the inert fluid 120 in the flaccid chamber 201.

As the inert fluid 120 egresses from the flaccid chamber 201, the blood 110 is allowed to enter the flaccid chamber 201. The blood 110 flows into the flaccid chamber 201 from the patient through the conduit 222 and through the inlet valve 214. The inert fluid inlet portion 210 as well as the blood inlet port 212 is open. The blood 110, progressing along the path of least resistance, passes only through the blood inlet port 212 into chamber 201 and not out the inert fluid inlet port 210 because fluid would need to flow the wrong way across a non-return valve 616.

FIG. 14 illustrates the pressure treatment pump 101 of the present invention at the end of the exhaust phase. The pressure treatment pump 101 is illustrated after being rotated counterclockwise 90 degrees back to the initial position. The flaccid chamber 201 is shown almost totally emptied of inert fluid 120. After inversion, the piston 640 is advanced slightly to insure that the inlet valve 214 is immersed in the inert fluid 120. The slugs 122 and 124 of the inert fluid 120 fills the outlet valve 220 and the inlet valve 214, respectively, with the inert fluid. The piston 430 in the pressurization system 400 can recede slightly to insure that the inlet valve 214 is immersed in the inert fluid 120. The valve 424 is closed.

In FIG. 15, the position of inlet valve 214 prohibits the additional flow of blood through the valve 214 from the conduit 222. The valve 220 is also closed. FIG. 15 illustrates the smaller inlet port 210 open to provide the passage of inert fluid 120 from the feed conduit 612 to the flaccid chamber 201. Then the high pressure valve 414 is opened to activate the high pressure supply 410.

The high pressure supply 410 charges the pressurization fluid 316. The pressurization fluid 316 applies pressure directly to the flaccid chamber 201. It is preferable that the pressure applied to the flaccid chamber 201 is isotropic. The application of isotropic pressure to the blood 110 in the flaccid chamber 201 prevents the damage of the red cells within the blood 110. The isotropic pressure applied to the blood 110, is sufficient in duration and intensity, will dissolve or crush gaseous bubbles within the blood 110. The isotropic pressure applied to the flaccid chamber 201 is advantageously between about 50 and about 1,000 psi. Also, the time duration of the isotropic pressure applied to the flaccid chamber 201 is advantageously approximately 1 to 30 seconds. However, greater pressures or longer durations of the pressures may be utilized if desired.

After the high pressure valve 414 is closed to terminate the pressure and the pressure is reduced, the outlet valve 220 opens, as indicated by the arrow in FIG. 15, to enable blood 110 to flow from the flaccid chamber 201, through the blood outlet port 218 in the valve 220, and into the conduit 502. The inlet valve 214 is positioned to allow only the flow of inert fluid through the feed conduit 612, into the inlet valve 214 through the smaller inlet port 210, and into the flaccid chamber 201. When the outlet valve 220 is opened, the slug 122, which encompassed the valve 220, acts under the force of gravity and flows down the interior 204 of the flaccid chamber 201. The slug 122 is withdrawn from the flaccid chamber 201 by the piston 640 being withdrawn in the chamber 650. The pump 101 is now about to repeat the cycle shown in FIGS. 10 through 15. Thus, FIG. 10 illustrates the blood 110 being exhausted from the flaccid chamber 201 by the inert fluid 120 which is activated by the piston 640 in the chamber 650.

As noted earlier, the blood pump 100/101 of the present invention can be termed a two-phase pump using one liquid to pump another liquid. Thus, the inert, heavier than blood, immiscible fluid is used as a liquid piston to pump the blood 110 out of the flaccid chamber 200, 201 and to draw the blood 110 into the flaccid chamber 200, 201. Any suitable heavy insoluble fluid can be used as the liquid piston. In the present case, it is preferred that fluorocarbons be used. The choice of fluorocarbon provides enhanced characteristics for the pump 100/101.

In the preferred embodiment of the present invention all of the interior components in direct contact with the blood 110 are covered with fluorocarbon. Thus, a coating of "Teflon", a fluorocarbon, can be used. The fluorocarbon used as the liquid piston and the fluorocarbon used to coat the interior surfaces of the pump 100 have such an affinity that a liquid film of the fluorocarbon is always maintained on the blood transferring surfaces. The liquid film of fluorocarbon prevents the blood from coming into direct contact with a solid surface. Microthrombus formation and other adverse blood effects are thus minimized.

The inlet valve 214 and outlet valve 220 of the flaccid chamber 201 can be any compatible valves. In the embodiment discussed above, the inlet valve 214 and the outlet valve 220 should be able to withstand sufficiently high pressure differentials to dissolve or crush gaseous bubbles in the blood. In any case, valve closure is effected only when the moving ports are immersed in fluorocarbon and never when the moving ports are engaged with blood. This procedure minimizes damaging and hemolysis of the blood.

In practicing the present invention, it is possible to utilize a combination of the pumps 100/101. The pumps 100/101 can be connected in series or in parallel depending on the flux of blood required. For example, if the time duration of the application of the isotropic pressure to the flaccid chamber 201 is sufficiently high, two pumps 100 can be used in parallel. When the first pump is in the exhaust phase, the second pump can be in the intake phase. Such a configuration of pumps would increase the pumping rate.

A method of the present invention for pressure treating blood comprises receiving the blood in a flaccid chamber 201, applying sufficient isotropic pressure to the flaccid chamber 201 to compress the blood adequately to dissolve or to crush the gaseous bubbles in the blood, and expelling the blood from the flaccid chamber 201. The step of applying sufficient isotropic pressure may involve applying a pressure of between about 50 to 1,000 pounds per square inch for a time duration of approximately 1 to 30 seconds.

A more detailed method embodiment of the present invention includes the step of pumping an inert, heavier than blood, immiscible fluid into a flaccid chamber 201. The movement of the fluid in the flaccid chamber 201 is stabilized and the flaccid chamber 201 is inverted to position the chamber outlet 220 below the chamber inlet 214, drawing the inert fluid from the flaccid chamber 201 thereby causing the blood to ingress the flaccid chamber 201 through the chamber inlet 214. The movement of the blood in the flaccid chamber 200, 201 is stabilized and pressure is applied to the flaccid chamber 201 isotropically for a sufficient time duration to dissolve or otherwise dissipate gaseous bubbles in the blood. The application of pressure to the flaccid chamber 201 is ceased and the flaccid chamber 201 is inverted to position the chamber inlet 214 below the chamber outlet 220. The fluid is pumped into the flaccid chamber 201, thereby purging the blood from the flaccid chamber 201.

Additional advantages and modifications will readily occur to those skilled in the art. The invention in its broader aspects is therefore not limited to the specific details, representative apparatus, and the illustrative examples shown in the description herein. Accordingly, departures may be made from the detail without departing from the scope and spirit of the disclosed general inventive concept.

What is claimed is:

1. Apparatus for the pressure treatment of blood comprising:
    (a) a flaccid chamber having an interior surface, exterior surface, an inlet for accepting blood, an outlet for expelling blood;
    (b) a pressure housing including pressure applying means for applying pressure isotropically to blood in said flaccid chamber;
    (c) means for introducing a physiologically inert fluid which is heavier than and immiscible with blood into said flaccid chamber so as to displace blood from said flaccid chamber; and
    (d) means for rotating said flaccid chamber in order to change the orientation of the inlet and outlet with respect to one another.

2. An apparatus as defined in claim 1 further comprising a valve associated with the inlet of said flaccid chamber and a valve associated with the outlet of said flaccid chamber for controlling the flow of blood to and from said flaccid chamber.

3. An apparatus as defined in claim 2 wherein said valves are encompassed by said pressure housing for preventing pressure differentials on said valves thereby preventing said valves from leaking during the application of isotropic pressure by said pressure housing.

4. An apparatus as defined in claim 1 wherein the isotropic pressure comprises between about 50 to about 1,000 pounds per square inch of pressure.

5. An apparatus as defined in claim 4 wherein the time duration of the isotropic pressure comprises approximately 1 to 30 seconds.

6. An apparatus as defined in claim 3 wherein said pressure housing further comprises a gas for transferring an isotropic pressure to the blood within said flaccid chamber.

7. An apparatus as defined in claim 6 wherein the circulating temperature of said gas corresponds to the temperature of the blood of the patient for maintaining the temperature of the pumped blood at the same temperature as the blood of the patient.

8. An apparatus as defined in claim 2 wherein said valves comprise ball valves.

9. An apparatus as defined in claim 1 wherein the interior surface of said flaccid chamber has such an affinity for said inert fluid to further comprise a liquid film of said inert fluid on the interior surface of said flaccid chamber.

10. An apparatus as defined in claim 1 wherein the interior surface of said flaccid chamber and all related interior components are covered with a synthetic fluorocarbon and said inert fluid comprises a fluorocarbon, such that a liquid film of the fluorocarbon is maintained on the interior surface of said flaccid chamber thereby preventing the direct contact of blood with the interior surface, minimizing blood trauma and reducing microthrombus formations.

11. An apparatus as defined in claim 1 wherein said flaccid chamber is a unitary single-use unit.

12. A method for pumping blood comprising the steps of:
    closing a blood outlet valve in fluid communication with a flexible chamber when said outlet valve is in contact with an inert fluid that is immiscible with blood;
    inletting blood into said flexible chamber through an inlet valve;
    filling the inlet valve with said inert fluid;
    closing said blood inlet valve when said inlet valve is in contact with said inert fluid; and
    displacing said blood from said chamber through said outlet valve by pumping said inert fluid into said chamber.

13. The method of claim 12 including the step of rotating said inlet and outlet valves to position the valve to be closed below the other valve.

14. The method of claim 12 including the step of applying an isotropic pressure to said blood in said chamber.

* * * * *